United States Patent
Wantink et al.

(10) Patent No.: US 6,179,810 B1
(45) Date of Patent: Jan. 30, 2001

(54) CATHETER WITH A FLEXIBLE AND PUSHABLE SHAFT

(75) Inventors: Kenneth Lee Wantink, Temecula; Jeong Soo Lee, Diamond Bar; Barbara Stamberg, Santa Clara, all of CA (US)

(73) Assignee: Advanced Cardiovascular Systems, Inc., Santa Clara, CA (US)

( * ) Notice: Under 35 U.S.C. 154(b), the term of this patent shall be extended for 0 days.

(21) Appl. No.: 09/375,720

(22) Filed: Aug. 17, 1999

(51) Int. Cl.⁷ .................................................. A61M 29/00
(52) U.S. Cl. ............................ 604/96; 606/108; 606/191
(58) Field of Search .............................. 604/508, 96, 526, 604/523, 524, 533, 280, 282, 167, 3, 264; 606/108, 194, 191

(56) References Cited

U.S. PATENT DOCUMENTS

| | | |
|---|---|---|
| 5,217,482 | 6/1993 | Keith . |
| 5,451,233 | 9/1995 | Yock . |
| 5,490,837 * | 2/1996 | Blaeser et al. .......................... 604/96 |
| 5,743,874 * | 4/1998 | Fischell et al. ......................... 604/96 |
| 5,792,144 * | 8/1998 | Fischell et al. ........................ 606/108 |
| 6,036,670 * | 3/2000 | Wijeratne et al. ...................... 604/96 |
| 6,056,719 * | 5/2000 | Mickley ................................. 604/96 |

* cited by examiner

*Primary Examiner*—Michael Buiz
*Assistant Examiner*—Anthony S. King
(74) *Attorney, Agent, or Firm*—Heller Ehrman White & McAuliffe LLP

(57) ABSTRACT

A catheter comprising an elongated shaft having a distal shaft section with a first portion having co-axially disposed lumens, and a second portion having laterally off-set, adjacent lumens. The adjacent-lumen portion of the distal shaft section is preferably disposed proximal to the co-axial lumen portion, and comprises a first tubular member secured to a second tubular member such that the longitudinal axis of the first tubular member is laterally off-set from the longitudinal axis of the second tubular member. The coaxial lumen portion extends distally from the distal end of the adjacent-lumen portion, and generally comprises an inner tubular member disposed within an outer tubular member. One embodiment of the invention is a balloon catheter having an inflatable dilatation balloon on a distal end thereof.

24 Claims, 4 Drawing Sheets

CATHETER WITH A FLEXIBLE AND PUSHABLE SHAFT

BACKGROUND OF THE INVENTION

This invention generally relates to catheters, and particularly intravascular catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy where the balloon of the dilatation catheter is positioned within the stenosis to be dilated. The balloon is then inflated with radiopaque liquid at relatively high pressures (generally 4–16 atmospheres) to dilate the stenosed region of the diseased artery. One or more inflations may be needed to effectively dilate the stenosis. Additionally, a stent may be implanted within the artery, typically by delivery to a desired location within the artery in a contracted condition on a balloon of a catheter which is similar in many respects to a balloon angioplasty catheter and expansion to a larger diameter by inflation of the balloon.

An essential step in effectively performing a PTCA procedure is properly positioning the balloon catheter at a desired location within the coronary artery. To properly position the balloon at the stenosed region, the catheter must have good pushability and flexibility, to be readily advanceable within the tortuous anatomy of the patient's vasculature. U.S. Pat. No. 5,300,085 shows a balloon dilatation catheter having a single lumen proximal section, a coaxial lumen distal section formed by an inner tubular member coaxially disposed within an outer tubular member, and a guidewire port at a transition region spaced a substantial distance from the proximal end of the catheter and about 10–15 centimeters from the distal extremity of the catheter. The transition region is formed by bonding the proximal end of the outer tubular member of the coaxial lumen distal section around a short section of the distal end of the proximal section and the proximal end of the inner tubular member of the coaxial lumen distal section. It has been found that the catheter shown in the U.S. Pat. No. 5,300,085 patent may, on occasion, have suboptimal pushability.

What has been needed is a catheter which is highly trackable within the patient's anatomy, with improved flexibility and pushability. The catheter of the present invention provides these and other advantages.

SUMMARY OF THE INVENTION

This invention is directed to a catheter comprising an elongated shaft having a distal shaft section with a first portion having an inner lumen and an outer lumen, and a second portion having a first lumen and a second lumen separate and laterally-off set from the first lumen. The first portion of the distal shaft section is preferably disposed distal to the second portion, so that hereafter, the first portion is referred to as the distal portion of the distal shaft section, and the second portion is referred to as the proximal portion of the distal shaft section. However, the first portion may be proximal to the second portion in alternative embodiments. The proximal portion of the distal shaft section is less flexible than the distal portion of the distal shaft section, so as to provide the distal shaft section with both improved flexibility and pushability.

The proximal portion of the distal shaft section generally has a first lumen having a longitudinal axis and a separate second lumen parallel to and laterally off-set from the longitudinal axis of the first lumen. In a presently preferred embodiment, the proximal portion comprises a first tubular member secured to a second tubular member such that the longitudinal axis of the first tubular member is laterally off-set from the longitudinal axis of the second tubular member. The distal portion of the distal shaft section generally comprises an inner tubular member disposed within an outer tubular member. The proximal portion of the distal shaft section is sufficiently long so that the catheter is provided with improved pushability without disadvantageously affecting the flexibility of the catheter shaft.

In a presently preferred embodiment, the catheter is a balloon catheter generally comprising an elongated catheter shaft having a relatively stiff proximal shaft section and a relatively flexible distal shaft section, and with an inflatable dilatation member on a distal section of the catheter. In accordance with the invention, the distal shaft section has a proximal portion having an inflation lumen laterally off-set from and parallel with a guidewire lumen, and a distal portion having a guidewire lumen co-axially disposed within an inflation lumen.

The catheter may be a rapid exchange type catheter, having a guidewire receiving lumen in a distal section of the catheter shaft, such as the catheters described in U.S. Pat. Nos. 5,451,233 and 5,743,875, incorporated by reference herein in their entireties. Typically, a rapid exchange catheter has a distal guidewire port in the distal end of the catheter, a proximal guidewire port spaced a relatively short distance proximally from the distal guidewire port and a relatively long distance from the proximal end of the catheter shaft, and a relatively short guidewire receiving lumen extending therebetween.

Alternatively, the catheter may be an over-the-wire type catheter having an elongated shaft with proximal and distal ends, a guidewire port in the proximal end, a guidewire port in the distal end, and a guidewire lumen extending therein. An example of over-the-wire type catheter design which may be used is described in U.S. Pat. No. 5,480,383, incorporated by reference herein in its entirety.

The catheter of the invention is highly pushable and flexible due to the distal shaft section having a proximal portion with laterally off-set lumens and a distal portion with inner and outer lumens. The flexible and pushable distal shaft section provides a catheter with excellent trackability, and allows easy advancement over a guidewire and maneuvering within the patient's tortuous anatomy, to position the operative portion of the catheter at a desired location within the patient. These and other advantages of the invention will become more apparent from the following detailed description of the invention and the accompanying exemplary drawings.

DETAILED DESCRIPTION OF THE INVENTION

Figure 1:
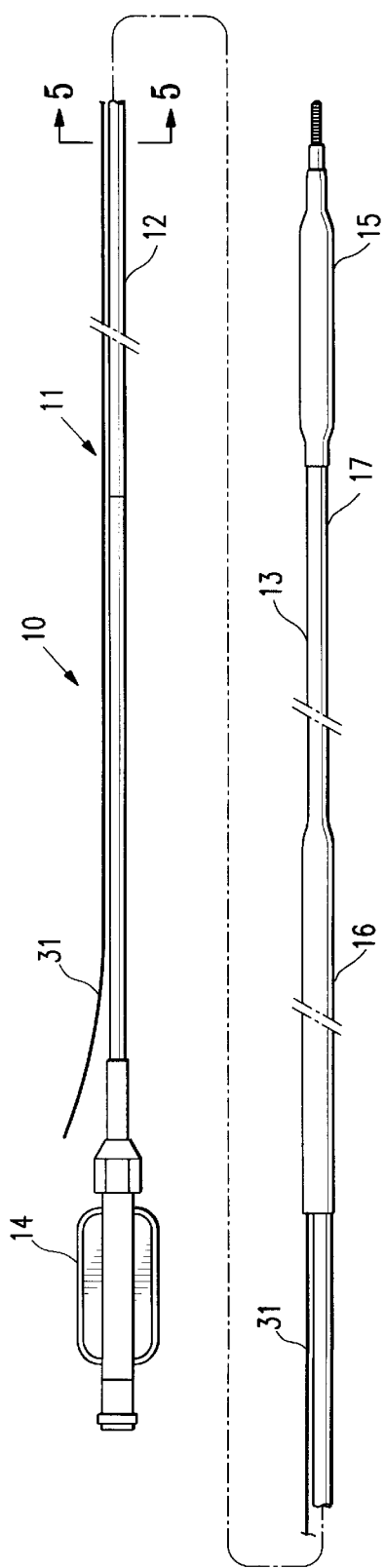
FIG. 1 is an elevational view of a catheter which embodies features of the invention.

FIG. 1 illustrates a first embodiment of a catheter 10 embodying features of the invention generally including an elongated shaft 11, a proximal shaft section 12, a distal shaft section 13, an adapter 14 mounted on the proximal end of the shaft, and an inflatable dilatation balloon 15 on the distal end of the shaft. The distal shaft section, illustrated in more detail in FIG. 2, has a proximal portion 16 having laterally off-set lumens and a distal portion 17 having inner and outer lumens.

Figure 2:
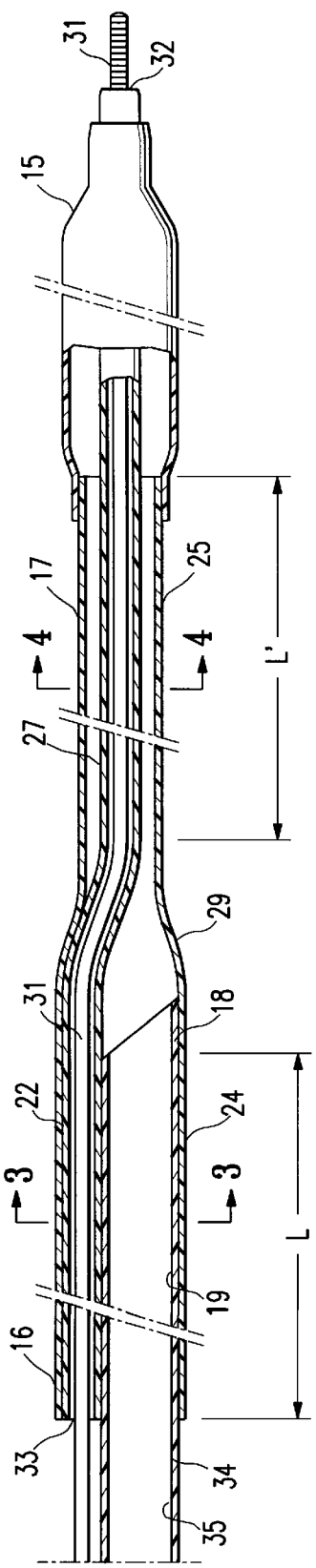
FIG. 2 is an enlarged view, partially in section, of a distal section of the catheter shown in FIG. 1.
Figure 3:
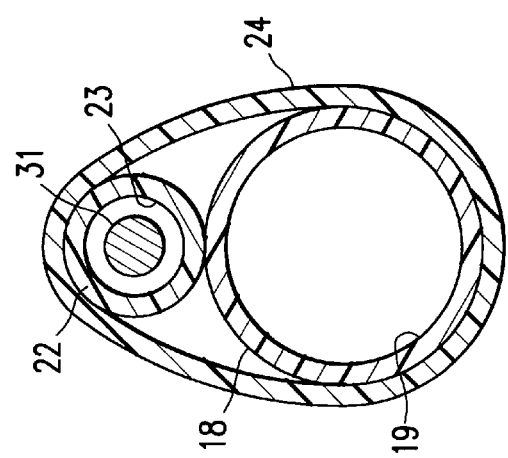
FIG. 3 is a transverse cross sectional view of the catheter shown in FIG. 2, taken along line 3—3.

In the embodiment illustrated in FIG. 2, the proximal portion 16 of the distal shaft section comprises a first tubular member 18 having proximal and distal ends and a first lumen 19 extending therein, a second tubular member 22 adjacent to the first tubular member and having proximal and distal ends and a second lumen 33 extending therein, and an outer tubular member 24 surrounding the first and second tubular members. As best illustrated in FIG. 3, showing a transverse cross section of the proximal portion 16 shown in FIG. 2, taken along line 3—3, the lumens of the first and second tubular members are separate and the longitudinal axis of the second tubular member is laterally off-set from and parallel to the longitudinal axis of the first tubular member. The outer tubular member 24 is tightly fit around the outside of the first and second tubular members. Additionally, a variety of suitable securing means, including heat and fusion bonds and adhesives (not shown) may be provided to secure the first and second tubular members together. The outer tubular member may be similarly secured to the first and second tubular members, and/or formed of suitable material so that it can be shrunk onto the first and second tubular members 18, 22, to form a liquid tight seal with respect to the same.

Figure 4:
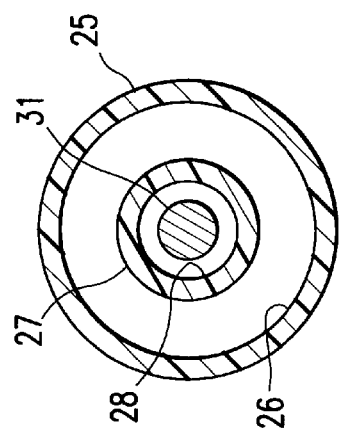
FIG. 4 is a transverse cross sectional view of the catheter shown in FIG. 2, taken along line 4—4.

As best shown in FIG. 4, illustrating a transverse cross section of the catheter shown in FIG. 2, taken along line 4—4, the distal portion 17 of the distal shaft section includes an outer tubular member 25 having proximal and distal ends and a third lumen 26 extending therein, and an inner tubular member 27 co-axially disposed within the outer tubular member 25 and having proximal and distal ends and a fourth lumen 28 extending therein. While the inner tubular member is shown co-axially disposed within the outer tubular member, it should be understood that the inner tubular member may be off centered within the outer tubular member. The outer tubular member 25 of the distal portion and the outer tubular member 24 of the proximal portion may be formed from a single tubular member, or alternatively, may be formed from separate tubular members joined together at the interface therebetween. Similarly, the proximal portion second tubular member 22 and the distal portion inner tubular member 27 may be formed from a single tubular member, or alternatively, from separate tubular members joined together at the interface therebetween. Thus, the distal shaft section proximal and distal portions are joined together or formed from single, continuous tubular members so that the first lumen 19 of the first tubular member is in fluid communication with the third lumen 26 of the outer tubular member, and the second lumen 23 of the second tubular member is in fluid communication with the fourth lumen 28 of the inner tubular member. In the embodiment illustrated in FIG. 2, the distal portion 17 of the distal shaft section 13 has a smaller outer diameter than the proximal portion 16 of the distal shaft section, however, in alternative embodiments (not shown) the outer diameter of the distal portion 17 may be equal to or greater than the outer diameter of the proximal portion 16.

In the embodiment illustrated in FIG. 2, transition region 29 is formed at the interface between the distal shaft section proximal and distal portions 16, 17. The proximal portion 16 second tubular member 22 extends a short distance beyond the distal end of the first tubular member 18 before the co-axial distal portion 17 begins.

The inner tubular member 27 extends through the interior of the inflatable dilatation balloon 15 to port 32 in the distal end of the catheter. The distal end of the inflatable dilatation balloon 15 is sealingly secured to the distal end of the inner tubular member. The proximal end of the balloon is sealingly secured to the distal end of the outer tubular member 25, or alternatively, the balloon and the outer tubular member 25 may be formed in a unitary construction as a single, continuous member. The interior of the balloon is in fluid communication with lumen 26 of the outer tubular member 25.

The length of the proximal and distal portions of the distal shaft section are indicated in FIG. 2, at lengths L and L', respectively. The proximal portion 16 of the distal shaft section has a length of at least about 3 centimeters, typically about 5 to about 20 centimeters, and preferably about 15 to about 20 centimeters. The distal portion 17 has a length of about 5 to about 20 centimeters. The length of the distal shaft section, from the proximal end of the proximal portion to the distal end of the distal portion, is generally about 30 to about 60 centimeters, and excluding the length of the distal shaft section extending distally of the proximal end of the balloon is generally about 20 to about 40 centimeters. In one embodiment, the proximal portion of the distal shaft section is at least about one half the length of the distal shaft section, or not less than the length of the distal portion.

In the embodiment illustrated in FIGS. 1–4, the second tubular member 22 and the inner tubular member 27 are configured to slidably receive a guidewire 31 therein. The guidewire receiving lumens 23, 28 extend between a distal guidewire port 32 in the distal end of the inner tubular member 27, and a proximal guidewire port 33 in the proximal end of the second tubular member 22. As shown in FIG. 1, the guidewire exits the catheter proximally from the guidewire port 33 and extends alongside and exteriorally of the proximal shaft section 12 to the proximal end of the catheter 10. In the embodiment illustrated in FIG. 2, the longitudinal axis of the second tubular member 22 is laterally off-set from the proximal shaft section. Thus, the guidewire 31 exits the port 33 laterally offset from and adjacent to the proximal shaft section.

Figure 5:
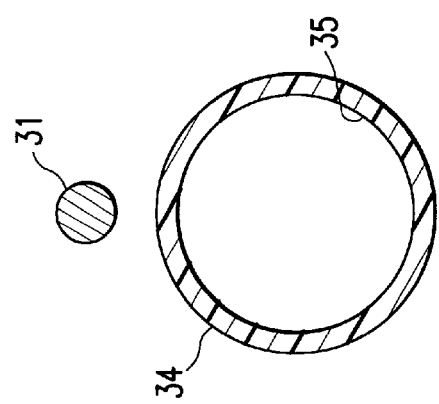
FIG. 5 is a transverse cross sectional view of the catheter shown in FIG. 2, taken along line 5—5.

The proximal shaft section 12 comprises a elongated tubular member 34 having a port in the distal end and a fifth lumen 35 in fluid communication with the first lumen 19 of the first tubular member 18 of the distal shaft section, as illustrated in FIG. 5, showing a transverse cross section of the catheter shown in FIG. 1, taken along line 5—5. Typically, the tubular member 34 of the proximal shaft section will be formed as a single, continuous member with the first tubular member 18 of the distal shaft section. Alternatively, the tubular member 34 may be a formed as a separate member joined to the proximal end of the first tubular member by a variety of suitable means including fusion bonds and adhesives.

Figure 6:
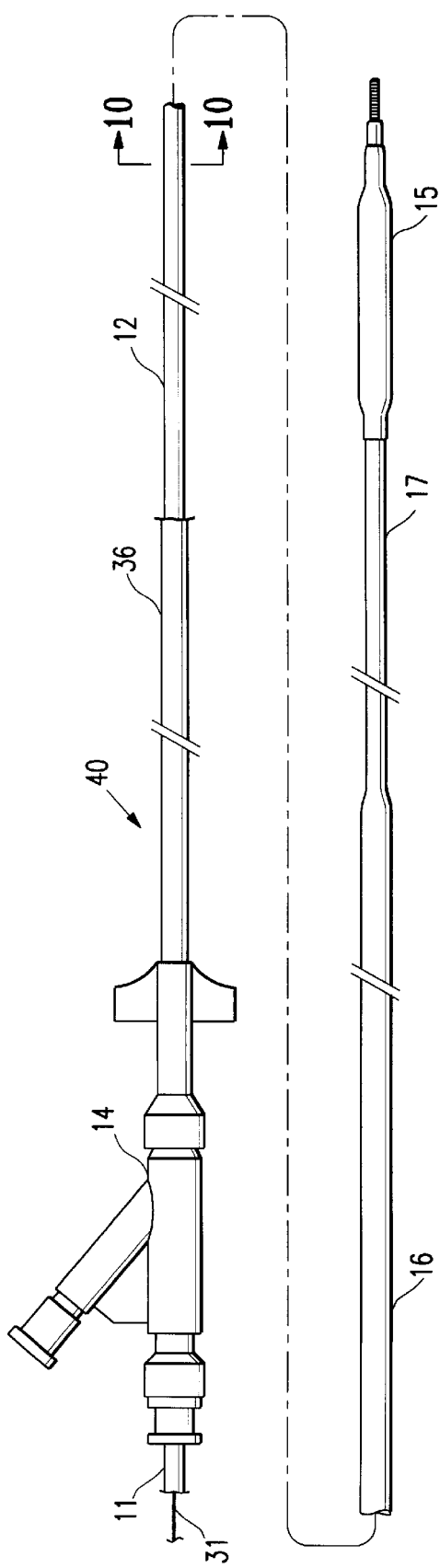
FIG. 6 is an elevational view of an alternative embodiment of the catheter of the invention, which embodies features of the invention.
Figure 7:
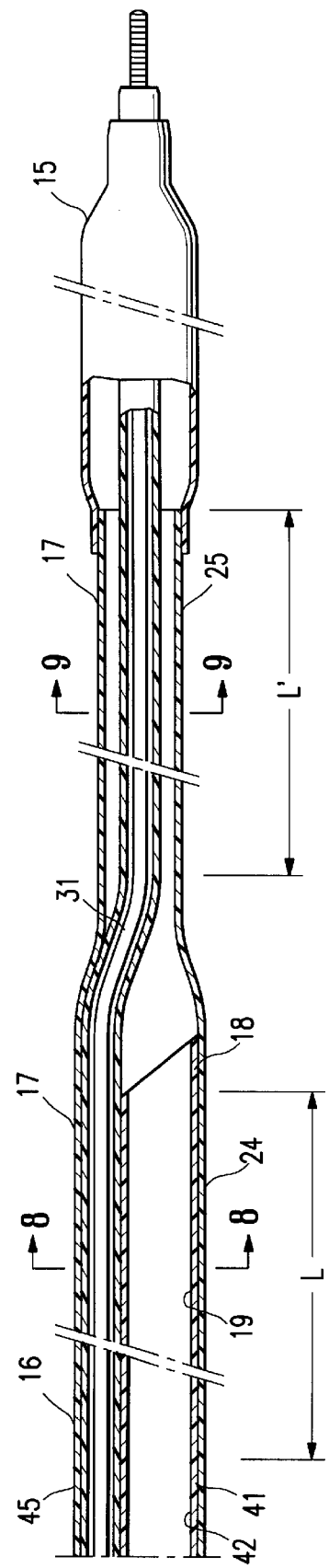
FIG. 7 is an enlarged view, partially in section, of a distal section of the catheter shown in FIG. 6.
Figure 9:
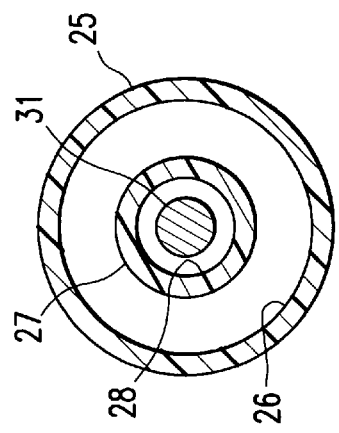
FIG. 9 is a transverse cross sectional view of the catheter shown in FIG. 7, taken along line 9—9.
Figure 8:
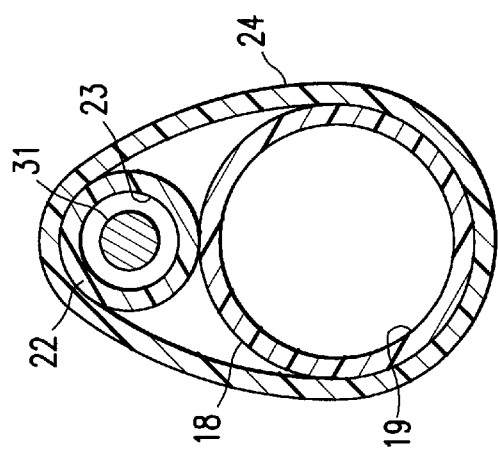
FIG. 8 is a transverse cross sectional view of the catheter shown in FIG. 7, taken along line 8—8.
Figure 10:
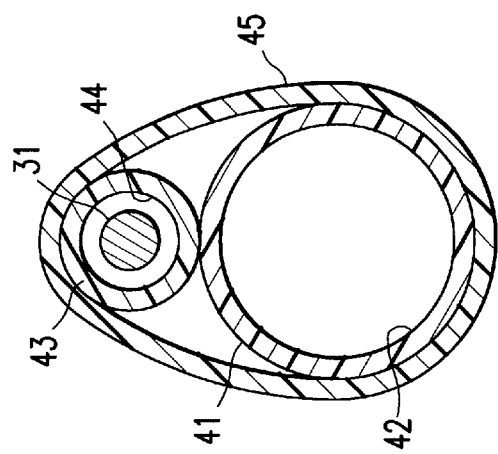
FIG. 10 is a transverse cross sectional view of the catheter shown in FIG. 6, taken along line 10—10.

In an alternative embodiment illustrated in FIG. 6, the catheter 40 has a proximal shaft section which includes a guidewire lumen 44 in fluid communication with the guidewire lumens 23, 28 of the distal shaft section, and a guidewire port in the proximal end of the proximal shaft section. As best shown in FIG. 7, illustrating an enlarged, longitudinal cross section of the distal end of the catheter of FIG. 6, the proximal shaft section comprises fifth tubular member 41 having a fifth lumen 42 in fluid communication with the first lumen 19 of the distal shaft section, and a sixth tubular member 43 with a sixth lumen 44 in fluid communication with the second lumen 23 of the distal shaft section. In the embodiment illustrated in FIG. 7, the fifth and sixth tubular members 41, 43 are longitudinally adjacent and laterally off-set from one another, similar to the first and second tubular members of the distal shaft section, with outer tubular member 45 in surrounding relation thereto. However, in an alternative embodiment (not shown) the sixth tubular member 43 may be co-axially disposed within the lumen 42 of the fifth tubular member 41, similar to the inner and outer tubular members of the distal shaft section. In accordance with the invention, the distal shaft section of the embodiment illustrated in FIGS. 6–10 is similar to the distal shaft section described above in relation to the embodiment illustrated in FIG. 1, as illustrated in FIGS. 8 and 9, showing transverse cross sections of the catheter shown in FIG. 6, taken along line 8—8 and 9—9, respectively. FIG. 10 illustrates a transverse cross section of the catheter shown in FIG. 6, taken along line 10—10. The catheter may be disposed within a guiding catheter 36 as illustrated in FIG. 6.

When the catheter of the invention is used in an angioplasty procedure, the guidewire 31 may be introduced into the balloon catheter 10,40 at the port 32 in the distal end of the inner tubular member 22 by a back loading technique. A guiding catheter 36 may be provided and the guidewire and balloon catheter of the invention advanced therein, by first advancing the guidewire ahead of the balloon catheter until it is in place within the vessel of the patient. The catheter 10,40 is then advanced over the guidewire until the balloon is properly positioned across the stenosis. The balloon can be inflated in a conventional manner by introducing inflation fluid through inflation lumen 35,42. After one or more inflations, the balloon is deflated and the catheter removed from the patient.

The length of the dilatation catheter is generally about 137 to about 145 centimeters, and typically about 140 centimeters for PTCA. The outer tubular member 25 of the distal portion of the distal shaft section has an outer diameter (OD) of about 0.028 to about 0.036 inch (0.70–0.91 mm) and an inner diameter (ID) of about 0.024 to about 0.035 inch (0.60–0.89 mm). The inner tubular member 27 of the distal portion of the distal shaft section has an OD from about 0.017 to about 0.026 inch (0.43–0.66 mm). The ID of the inner tubular member 27 will usually be determined by the diameter of the guidewire which is to be used with the catheter, which may range from about 0.011 to about 0.018 inch (0.28–0.38 mm).

The first tubular member 18 of the proximal portion of the distal shaft section has an outer diameter (OD) of about 0.25 to about 0.34 inch (0.63–0.87 mm) and an inner diameter (ID) of about 0.012 to about 0.022 inch (0.30–0.56 mm). The second tubular member 22 of the proximal portion of the distal shaft section has an OD from about 0.017 to about 0.026 inch (0.43–0.66 mm), and an ID of about 0.011 to about 0.019 inch (0.28–0.48 mm). The diameters of the inner tubular member lumen and the second tubular member lumen should be about 0.001 to about 0.005 inch (0.02–0.13 mm) larger than the OD of the guidewire.

The various catheter components may be formed of conventional materials. For example, the catheter shaft sections may be formed of polyether block amides such as PEBAX 55-72D, polyamides such as Nylon 12, and Grylamide L-25.

While the present invention has been described herein in terms of certain preferred embodiments, those skilled in the art will recognize that modifications and improvements may be made without departing form the scope of the invention. For example, while the catheter illustrated in FIGS. 1 and 6 has an adjacent lumen portion having an oblong transverse cross section, other cross sectional configurations may be used, such as circular cross sections.

What is claimed is:

1. A catheter having an elongated shaft, comprising:
   a) a distal shaft section which has
      a proximal portion at least 3 centimeters in length with a first lumen having a longitudinal axis, and a separate second lumen parallel to and laterally off-set from the longitudinal axis of the first lumen and an outer tubular member surrounding the first and second lumens therein; and
      a distal portion having an outer tubular member and an inner tubular member disposed within the outer tubular member defining a third annular lumen between the inner and outer tubular member which is in fluid communication with the first lumen of the proximal portion, the inner tubular member having a fourth lumen in fluid communication with the second lumen of the proximal portion; and
   b) a proximal shaft section which has a distal end, at least one port in the distal end, and a fifth lumen extending to the port in the distal end.

2. The catheter of claim 1 wherein the proximal portion of the distal shaft section comprises
   a) a first tubular member defining the first lumen; and
   b) a second tubular member defining the second lumen, and being juxtaposed, at least in part, with the first tubular member.

3. The catheter of claim 2 wherein the distal shaft section includes a distal port at a distal end of the inner tubular member in fluid communication with the fourth lumen therein.

4. The catheter of claim 3 wherein the distal shaft section includes a proximal port at a proximal end of the second tubular in fluid communication with the second lumen therein.

5. The catheter of claim 2 wherein a longitudinal axis of the second tubular member is laterally off-set from the proximal shaft section.

6. The catheter of claim 1 wherein the length of the distal shaft section is about 30 to about 60 centimeters.

7. The catheter of claim 6 wherein the length of the proximal portion of the distal shaft section is at least about 15 to about 20 centimeters.

8. The catheter of claim 1 wherein the length of the proximal portion of the distal shaft section is about 5 to about 20 centimeters.

9. The catheter of claim 1 wherein a length of the distal portion of the distal shaft section is about 5 to about 20 centimeters.

10. The catheter of claim 1 wherein the length of the proximal portion of the distal shaft section is not less than a length of the distal portion of the distal shaft section.

11. The catheter of claim 1 including a balloon on the distal shaft section having a proximal end, a distal end, and an interior in fluid communication with the first lumen of the proximal portion and the third lumen of the distal portion of the distal shaft section.

12. The catheter of claim 1 wherein the proximal shaft section comprises a tubular member defining the fifth lumen in fluid communication with the first lumen of the proximal portion and the third lumen of the distal portion of the distal shaft section.

13. The catheter of claim 1 wherein the fifth lumen of the proximal shaft section is in fluid communication with the first lumen of the proximal portion and the third lumen of the distal portion of the distal shaft section, and the proximal shaft section includes a sixth lumen in fluid communication with the second lumen of the proximal portion and the fourth lumen of the distal portion of the distal shaft section.

14. A catheter having an elongated shaft, comprising:
   a) a proximal shaft section having a proximal end, a distal end, a port in the distal end, and an inflation lumen extending therein;
   b) a distal shaft section having a proximal end and a distal end, which has
      a proximal portion at least 3 centimeters in length with a first tubular member having an inflation lumen having a longitudinal axis, a second tubular member having a guidewire-receiving lumen having a longitudinal axis laterally off-set from the longitudinal axis of the inflation lumen, and an outer tubular member in surrounding relation to the first and second tubular members; and
      a distal portion with an outer tubular member and an inner tubular member disposed within the outer tubular member and defining an inflation lumen between the inner and outer tubular members which is in fluid communication with the inflation lumen of the proximal portion, the inner tubular member having a guidewire-receiving lumen in fluid communication with the guidewire-receiving lumen of the proximal portion; and
   c) a balloon on the distal shaft section, having a proximal end on a distal end of the outer tubular member of the distal portion, a distal end on a distal end of the inner tubular member of the distal portion, and an interior in fluid communication with the inflation lumens of the proximal and distal shaft sections.

15. The catheter of claim 14 wherein the distal portion of the distal shaft section is more flexible than the proximal portion of the distal shaft section.

16. The catheter of claim 15 wherein the distal shaft section is more flexible than the proximal shaft section.

17. The catheter of claim 16 wherein the length of the proximal portion of the distal shaft section is about 5 to about 20 centimeters.

18. The catheter of claim 15 wherein the distal shaft section length is about 30 to about 60 centimeters.

19. The catheter of claim 18 wherein the length of the proximal portion of the distal shaft section is at least about 15 to about 20 centimeters.

20. The catheter of claim 14 wherein the distal shaft section includes a proximal guidewire port in a proximal end of the second tubular member, and a distal guidewire port in a distal end of the inner tubular member.

21. The catheter of claim 14 wherein the proximal shaft section includes a guidewire-receiving lumen in fluid communication with the guidewire-receiving lumens in the distal shaft section.

22. The catheter of claim 14 wherein the outer tubular member secures the first and second tubular members together.

23. The catheter of claim 14 wherein the length of the proximal portion of the distal shaft section is not less than a length of the distal portion of the distal shaft section.

24. The catheter of claim 14 wherein the inner tubular member is co-axially disposed within the outer tubular member.

\* \* \* \* \*

UNITED STATES PATENT AND TRADEMARK OFFICE
CERTIFICATE OF CORRECTION

PATENT NO.    : 6,179,810 B1                                                        Page 1 of 1
DATED         : January 30, 2001
INVENTOR(S)   : Kenneth Lee Wantink et al.

It is certified that error appears in the above-identified patent and that said Letters Patent is hereby corrected as shown below:

<u>Column 6,</u>
Line 23, after "axis,", delete "and".

Signed and Sealed this

Fifteenth Day of October, 2002

Attest:

Attesting Officer

JAMES E. ROGAN
*Director of the United States Patent and Trademark Office*